United States Patent [19]
Haffner et al.

[11] Patent Number: 5,419,775
[45] Date of Patent: May 30, 1995

[54] SYRINGE FLANGE ADAPTER AND METHOD

[75] Inventors: David S. Haffner, Mission Viejo; Kenneth E. Kadziauskas, Laguna Niguel, both of Calif.

[73] Assignee: Allergan, Inc., Irvine, Calif.

[21] Appl. No.: 182,930

[22] Filed: Jan. 18, 1994

[51] Int. Cl.⁶ ............................................. A61M 5/00
[52] U.S. Cl. .................................... 604/227; 604/187
[58] Field of Search ............... 604/227, 220, 218, 187, 604/232

[56] References Cited
U.S. PATENT DOCUMENTS

| | | | |
|---|---|---|---|
| 2,551,339 | 5/1951 | Ryan et al. | 604/218 |
| 2,823,675 | 2/1958 | Sciurba | 604/227 |
| 4,068,661 | 1/1978 | Hennings | 604/227 |
| 4,291,695 | 9/1981 | Bekkering et al. | 604/227 X |
| 4,540,405 | 9/1985 | Miller et al. | 604/232 |
| 4,643,724 | 2/1987 | Jobe | 604/232 |
| 5,282,792 | 2/1994 | Imbert | 604/227 X |

FOREIGN PATENT DOCUMENTS 20266 12/1929 Netherlands .......................... 604/227

Primary Examiner—John D. Yasko
Attorney, Agent, or Firm—Gordon L. Peterson

[57] ABSTRACT

A syringe comprising a barrel having a longitudinal passage extending through the barrel and a plunger slidable in the passage of the barrel. The barrel has connector adjacent one end of the barrel for attaching a cannula to the barrel and a flange adjacent the other end of the barrel. An adapter having a passage extending through it is mounted on the barrel with the adapter engaging the flange of the barrel. The adapter extends radially beyond the flange to form finger pads.

2 Claims, 2 Drawing Sheets

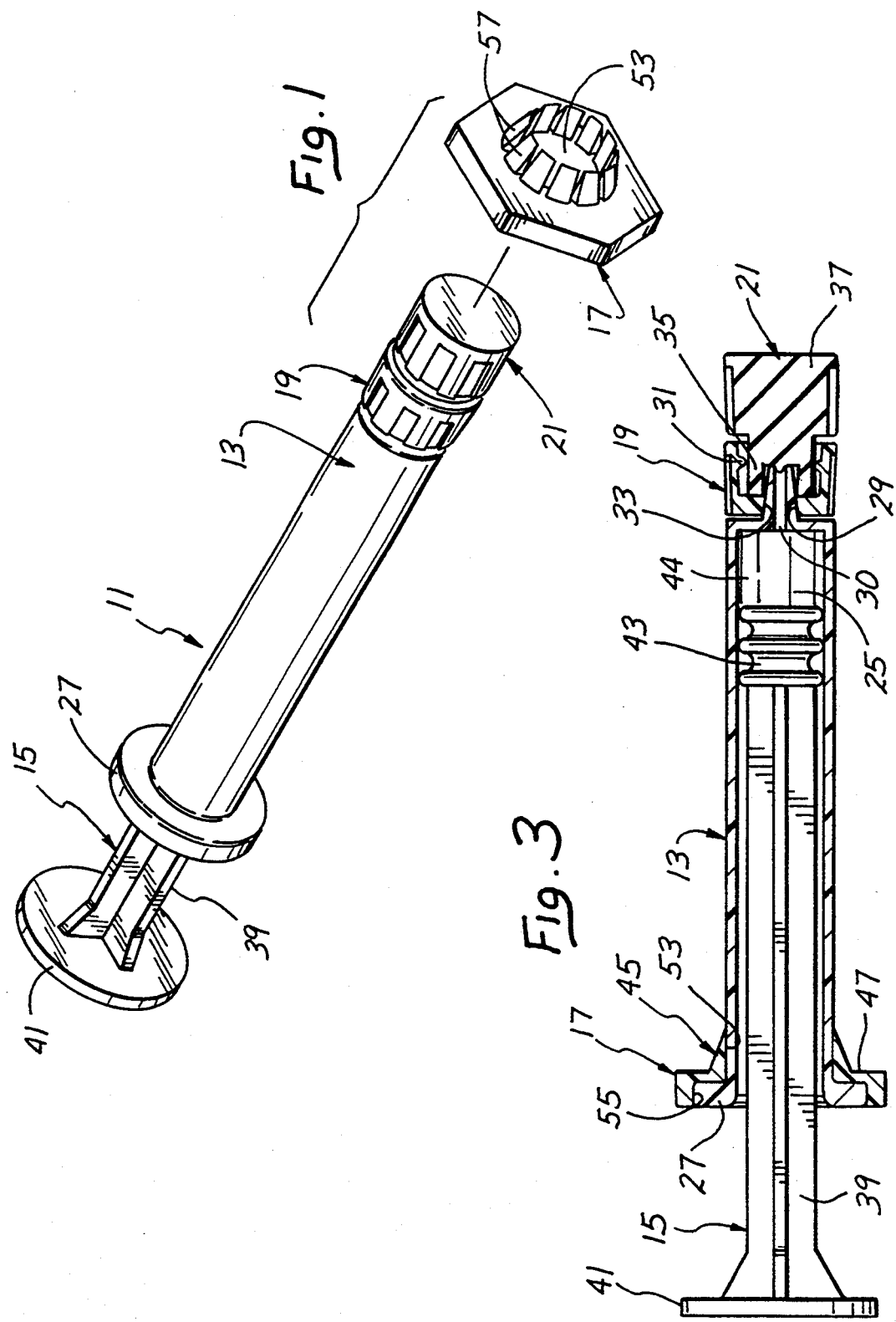

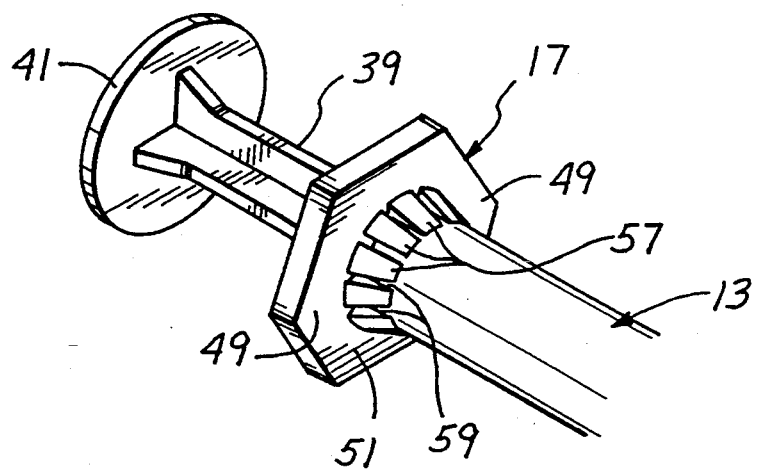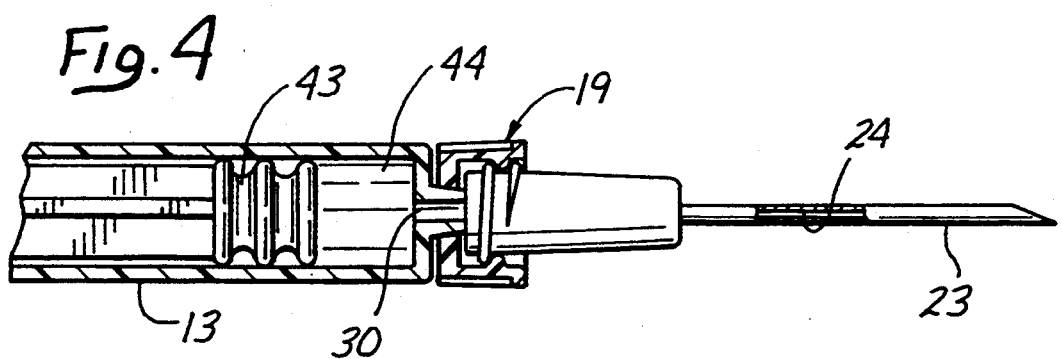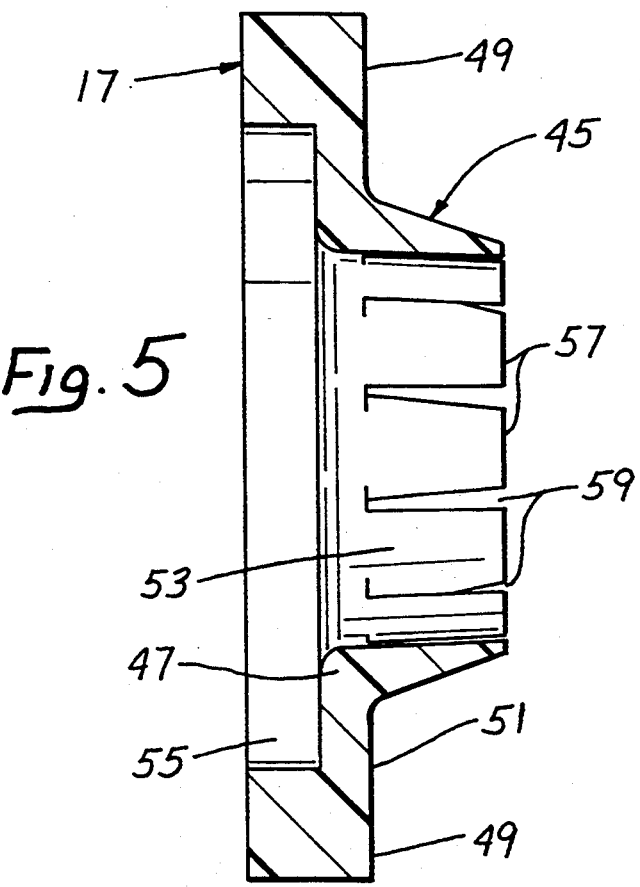

SYRINGE FLANGE ADAPTER AND METHOD

FIELD OF THE INVENTION

This invention relates to an adapter for a syringe and more particularly to an adapter which facilitates use of the syringe in extruding viscous material through a relatively small orifice.

BACKGROUND OF THE INVENTION

It is sometimes necessary to expel viscous material from a syringe through a relatively small orifice. One example is in cataract surgery where a viscous material, such as sodium hyaluronate, is injected into the capsular bag to protect regions of the eye as the natural lens is being removed. This viscous material is manually injected utilizing a syringe which is coupled to a cannula which has a relatively small diameter passage extending through it.

One problem with syringes of this type is that it is difficult to generate sufficient force to extrude the viscous material through the small diameter passage of the cannula. One way to solve this problem would be to increase the diameter of the passage in the cannula. However, for applications such as eye surgery, this is not desirable because of the need to use instruments of the smallest possible size in the eye.

Another possible solution would be to utilize a syringe having a smaller cross sectional area bore which could generate a higher pressure on the viscous material. However, the commercially available smaller bore syringes known to either of us do not have a strong connector, such as a Luer lock fitting for coupling the syringe to the cannula or are otherwise not as desirable for the injection of viscous material into the capsular bag. A strong connector is essential because with the relatively high pressures generated, a weak connector may fail in which event the cannula becomes a missile which can shoot into the patient's eye causing injury.

SUMMARY OF THE INVENTION

This invention provides a syringe which generally overcomes the problems noted above. With this invention, a larger bore syringe barrel having an adequate volume to contain the viscous material and a Luer lock fitting is utilized. An adapter is used to facilitate generation of adequate extrusion force to cause the viscous material to flow through the cannula.

The features of this invention may be incorporated into a syringe which comprises a barrel having a longitudinal passage extending through the barrel and a plunger slidable in the passage of the barrel. The barrel has a connector adjacent one end of the barrel for attaching a cannula to the barrel and a flange adjacent another end of the barrel. The plunger has a pressure pad outside the passage of the barrel adjacent one end of the plunger.

In order to mount the adapter on the barrel of the syringe, the adapter has a passage extending through it which is adapted to receive the barrel. The adapter is engageable with the flange of the barrel and the adapter extends radially beyond the flange to form finger pads when the adapter is on the barrel and engaging the flange. With this construction, the plunger is pushed by the thumb or palm of the user while the relatively wide adapter is retained by the index and middle fingers of the same hand. This enables the generation of much higher force than if the barrel were manually retained only by the conventional relatively short flange of the barrel.

Another feature of the invention is that the adapter includes a resilient section which performs several important functions. First, in many cases the connector, which is ordinarily a Luer lock fitting, is larger radially than the barrel. In this event, the resilient section resiliently flexes to allow the adapter to slide over the connector to mount the adapter on the barrel. Once on the barrel, the resilient section resiliently grips the barrel to tend to maintain the adapter in position on the barrel. The resilient section also positively resists sliding of the adapter off of the end of the barrel which contains the connector. Although the resilient section my take different forms, preferably it includes a plurality of resilient spring fingers.

It is desirable to sterilize the syringe with the adapter in place on the barrel. To help accomplish this, the adapter preferably cooperates with the barrel of the syringe to provide a flow path for sterilization gas, such as ethylene oxide, to flow to the flange of the barrel. The flow path may be provided, for example, by circumferentially spacing the fingers and by providing a radial clearance between other portions of the adapter and the barrel. In a preferred construction, the adapter includes a collar which extends radially beyond the flange to form the finger pads, and in this event, the collar may loosely receive the barrel to provide the desired radial clearance for sterilization gas. The adapter may also have a plurality of flat regions to reduce the likelihood of the syringe being able to roll on a flat surface.

The adapter is particularly adapted for use with a syringe of the type having a connector, such as a Luer lock fitting, on the barrel. However, it may also be used with syringes which do not have a connector for a cannula on the barrel.

Another advantage of the resilient section is in making the syringe. Thus, the adapter can be slid over the connector and onto the barrel to place the collar in engagement with the flange with the resilient section resiliently flexing to allow the adapter to slide over the connector and with the resilient section resiliently gripping the barrel when the collar engages the flange.

Preferably the pressure pad provided by the plunger has a smoothly curved concave end surface outside the barrel. The concave end surface is adapted to be engaged by a thumb of the user, and the concave shape provides a configuration which can be comfortably engaged by the thumb of the user. This is important to enable a high force to be applied to the plunger with relative ease.

The syringe of this invention can be used with various flowable materials; however, it is particularly adapted for use with a material which is an effective protectant against ocular surgical trauma such as a viscoelastic component, Preferred viscoelastic materials include hyaluronate based materials. Another preferred material which may or may not be regarded as viscoelastic is hydroxypropylmethylcellulose (HPMC).

The invention, together with additional features and advantages thereof may best be understood by reference to the following description taken in connection with the accompanying illustrative drawings.

BRIEF DESCRIPTION OF THE DRAWINGS

FIG. 1 is a perspective view of a syringe constructed in accordance with the teachings of this invention prior to sliding of the adapter over the connector and onto the barrel.

FIG. 2 is a fragmentary perspective view similar to FIG. 1 with the adapter in place on the barrel of the syringe and in contact with the flange of the barrel.

FIG. 3 is an axial sectional view of the syringe.

FIG. 4 is a fragmentary, axial sectional view with the tip cap removed and a cannula attached to the Luer lock fitting.

FIG. 5 is an axial sectional view of the adapter.

DESCRIPTION OF THE PREFERRED EMBODIMENT

FIG. 1 shows a syringe 11 which generally comprises a barrel 13, a plunger 15, an adapter 17, a connector in the form of a Luer lock fitting 19 and a tip cap 21. The syringe 11 may also be considered as including a cannula 23 (FIG. 4). The cannula has a small diameter passage 24 which may be, for example about 0.008 inch to about 0.020 inch in diameter.

The barrel 13 may be of a common commercially available type which includes a cylindrical, longitudinal passage 25 extending through the barrel, and a circular flange 27 at the proximal end of the barrel. The distal end of the barrel 13 has an axially extending tip section 29 which is adapted for connection to the Luer lock fitting 19. The tip section 29 has an axial bore 30 extending through the tip section. Except for the flange 27 and the tip section 29, the barrel 13 is cylindrical. The barrel 13 is preferably integrally constructed of glass.

The Luer lock fitting 19 is also conventional and commercially available. As such, it includes an internally threaded socket 31 (FIG. 3) and an aperture 33 in its back wall for receiving the tip section 29 to which it is suitably attached as a mechanical interlock commonly used for Luer lock fittings. The Luer lock fitting 19 may also be constructed of polycarbonate.

The tip cap 21 is also a commercially available component and is provided for the purpose of sealing off the bore 30 in the tip section 29 to maintain sterility within the passage 25. The tip cap 21 is constructed of an elastomeric material and it includes an annular sealing skirt 35 and a knob 37 for use in installing and removing the tip cap.

The plunger 15 includes an elongated shank 39 which, in this embodiment has a plus or cross-shaped cross section and a pressure pad 41 at the proximal end of the shank 39. The plunger 15 may also be considered as including a conventional resilient piston 43 coupled to the distal end of the shank 39 and cooperable with the passage 25 to provide a pumping type function common to syringes. Thus, by moving the plunger 15 proximally, the piston 43 can draw a flowable material 44 into the passage 25 and by moving the plunger distally, the flowable material can be expelled from the passage 25 through the cannula 23 (FIG. 4). The pressure pad 41 is relatively large and may be, for example, about 0.74 inch in diameter. Although the plunger 15 may be constructed of various different materials, polycarbonate is preferred.

The adapter 17, which may also be constructed of polycarbonate, includes a resilient section 45 and a collar 47 which extends radially outwardly to form finger pads 49 on opposite sides of the adapter. More specifically, the finger pads 49 are simply diametrically opposed portions of an annular surface 51 which surrounds the resilient section 45.

The adapter 17 also includes a bore or passage 53 extending axially completely through the adapter and a counterbore 55 of circular configuration sized and adapted to receive the flange 27. Although the resilient section 45 may be of various different constructions, in this embodiment it includes a plurality of resilient spring fingers 57 which are spaced circumferentially by axially extending slots 59. As shown in FIG. 5, the fingers 57 taper such that they become progressively thinner in their radial dimension as they extend distally.

As shown in FIG. 3, the passage 53 through the adapter is adapted to receive the barrel 13 to mount the adapter on the barrel. The adapter 17 can be positioned in engagement with the flange 27 of the barrel 13 with the counterbore 55 receiving the flange as shown in FIG. 3. In this position, the adapter 17 extends radially beyond the flange 27 to provide the finger pads 49 which can be engaged by the index and middle fingers of the user when the thumb of the user presses on the thumb pad 41.

The resilient fingers 57 perform several important functions. For example, the adapter 17 can be assembled onto the barrel 13 by pushing the adapter over the tip cap 21 and the Luer lock fitting 19. In this regard, the Luer lock fitting 19 may be, and typically is, larger radially than the barrel 13. However, as clearly shown in FIGS. 1 and 3, the fitting 19 is not larger radially than the flange 27 and so more specifically the fitting 19 is larger radially than a main body portion of the barrel which may include all of the barrel except the flange 27. In this event, the resilient fingers 57 resiliently flex radially outwardly to allow the adapter to slide over the fitting 19 to mount the adapter on the barrel 13.

Once in position on the barrel 13, the fingers 57 resiliently grip the barrel to frictionally retard sliding movement of the adapter 17 along the barrel 13. In addition, the fingers 57 are engageable with the fitting 19 to positively resist sliding of the adapter 17 off of the connector 19.

Although the syringe 11 may be used with a variety of flowable materials 44, it is particularly adapted to be used with a sodium hyaluronate based material such as a sodium hyaluronate solution sold under the trademark Vitrax by Allergan, Inc. of Irvine, Calif. As indicated above, this material is injected into the posterior capsule of the eye during ophthalmic surgery in which the natural lens of the eye is being removed. Consequently, the syringe 11 may be sold with the passage 25 filled with the material 44 which may be a viscous flowable liquid, such as Vitrax or another hyaluronate based material.

Because the syringe is to be used in a medical context, it must be sterilized, and this is typically carried out using ethylene oxide gas. With the adapter 17 receiving the flange 27 in the counterbore 55, it is important to provide a flow path for sterilization gas to flow to the flange. Although this could be accomplished in different ways, in this embodiment, the flow path is provided by the slots 59 between the resilient fingers 57 and by mounting the collar 47 on the barrel 13 in a non-sealing relationship so that the sterilization gas can pass through the slots 59 and the unsealed interface between the collar 47 and the barrel 13.

In use of the syringe 11, the tip cap 21 is removed from the fitting 19 and the cannula 23 is attached to the fitting. The material 61 in the passage 25 can then be expelled through the small diameter passage 24 in the cannula 23 by moving the plunger 15 distally in a conventional manner. The larger area provided by the finger pads 49 and the pressure pad 41 facilitates the manual application of significant force to the plunger 15. Consequently, the plunger can be advanced to bring about movement or extrusion of the viscous material 61 through the small diameter passage 24 of the cannula 23.

Although an exemplary embodiment of the invention has been shown and described, many changes, modifications and substitutions may be made by one having ordinary skill in the art without necessarily departing from the spirit and scope of this invention.

We claim:

1. A syringe comprising:
   a barrel having a longitudinal passage extending through the barrel and a flange;
   a connector adjacent one end of the barrel for attaching a cannula to the barrel and said flange being adjacent another end of the barrel;
   a plunger slidable in the passage of the barrel to expel flowable material from the barrel and having a pressure pad outside the passage adjacent one end of the plunger;
   an adapter having a passage extending through the adapter which is adapted to receive the barrel, said adapter including a collar extending around the barrel radially beyond the flange to form finger pads and a plurality of circumferentially spaced spring fingers extending distally of the collar for gripping the barrel, said fingers tapering such that they become progressively thinner in their radial dimension as they extend distally; and
   said fingers being engageable with the connector to positively resist sliding of the adapter off of the connector.

2. A syringe comprising:
   a barrel having a longitudinal passage extending through the barrel and a radially outwardly extending annular flange;
   a connector adjacent one end of the barrel for attaching a cannula to the barrel, said flange being adjacent another end of the barrel and having a forward face facing said one end of the barrel;
   a plunger slidable in the passage of the barrel to expel flowable material from the barrel and having a pressure pad outside the passage adjacent one end of the plunger;
   an adapter having a passage extending through the adapter and a counterbore of circular configuration, said adapter being shorter than said barrel, said passage of the adapter being sized and adapted to allow the adapter to be slid over said connector and said one end of the barrel but not over the flange to the forward face of the flange, said counterbore being sized and adapted to receive the flange, said adapter including a collar extending radially beyond the flange to form finger pads; and
   said adapter including a resilient section adapted to be moved over the connector onto the barrel and for resiliently gripping the barrel to frictionally retard sliding movement along the barrel.

* * * * *